United States Patent [19]

Beers

[11] Patent Number: 4,987,778
[45] Date of Patent: Jan. 29, 1991

[54] COMPARATIVE TEMPERATURE COMPENSATING SPECIFIC GRAVITY TEST APPARATUS

[75] Inventor: Howard L. Beers, North Fort Myers, Fla.

[73] Assignee: HF Scientific, Inc., Ft. Myers, Fla.

[21] Appl. No.: 387,859

[22] Filed: Jul. 31, 1989

[51] Int. Cl.⁵ ............................................. G01N 9/10
[52] U.S. Cl. ........................................ 73/449; 73/440
[58] Field of Search ......................... 73/444, 448, 449; 116/215, 228

[56] References Cited

U.S. PATENT DOCUMENTS

| | | | |
|---|---|---|---|
| 1,335,253 | 3/1920 | Midgley | 73/448 |
| 3,808,893 | 5/1974 | Jinno et al. | 73/449 |
| 4,338,817 | 7/1982 | Callahan | 73/448 |
| 4,473,530 | 9/1984 | Villa-Real | 73/863.52 |
| 4,590,800 | 5/1986 | Shimoda | 73/449 |

Primary Examiner—John Chapman
Attorney, Agent, or Firm—William E. Noonan

[57] ABSTRACT

A comparative temperature compensating specific gravity test apparatus is disclosed including an indicator float element that has a predetermined specific gravity and is freely suspended in a homogeneous test liquid. The float element includes pliable, sealed container that is substantially free of contained gas and a reference liquid that fills the container. The reference liquid has a thermal expansion characteristic which is substantially the same as that of the test liquid. The container has a mass which is negligible relative to the mass of the reference liquid. The float element is monitored in the test liquid such that floating of the float element indicates that the test liquid has at least the predetermined specific gravity and sinking of the float element indicates that the test liquid has less than the predetermined specific gravity.

23 Claims, 2 Drawing Sheets

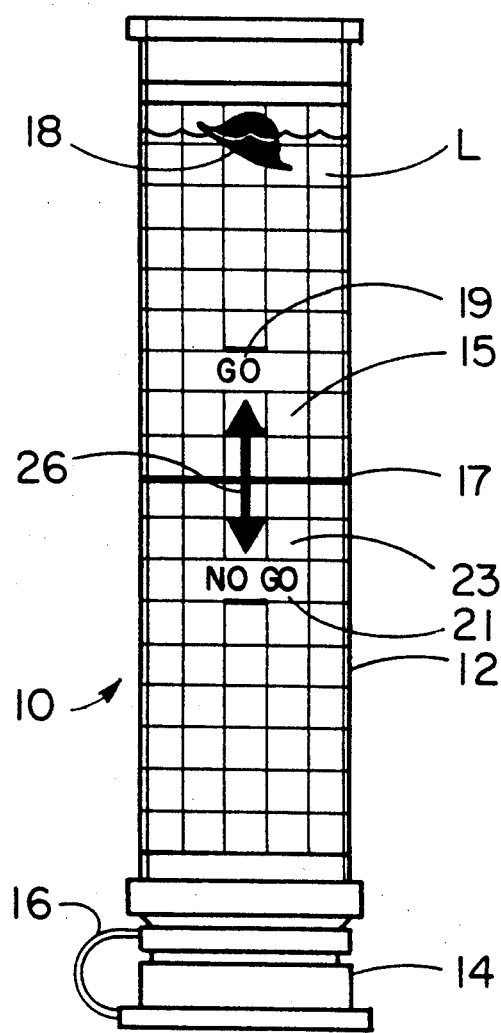
FIG. 2
FIG. 3
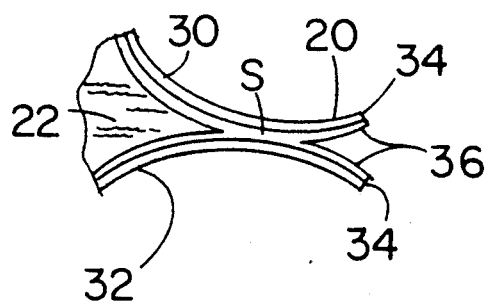
FIG. 4
FIG. 1

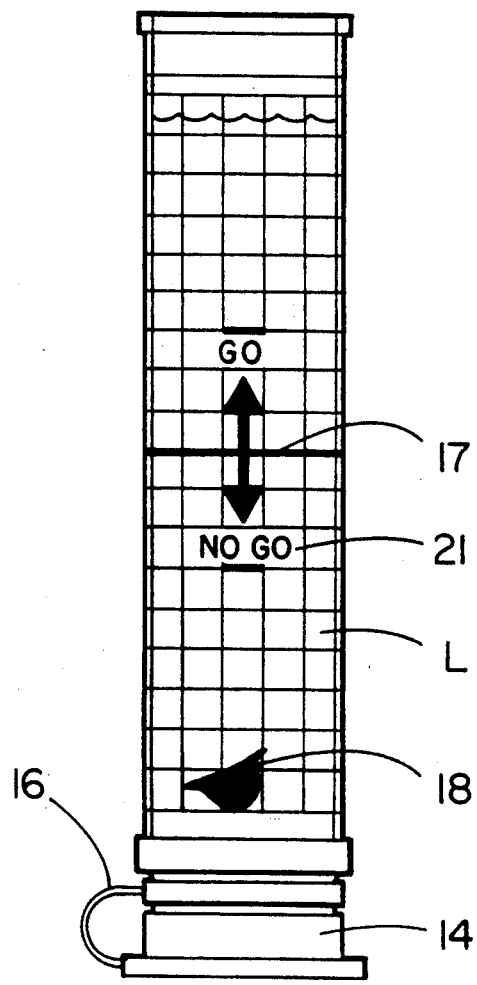
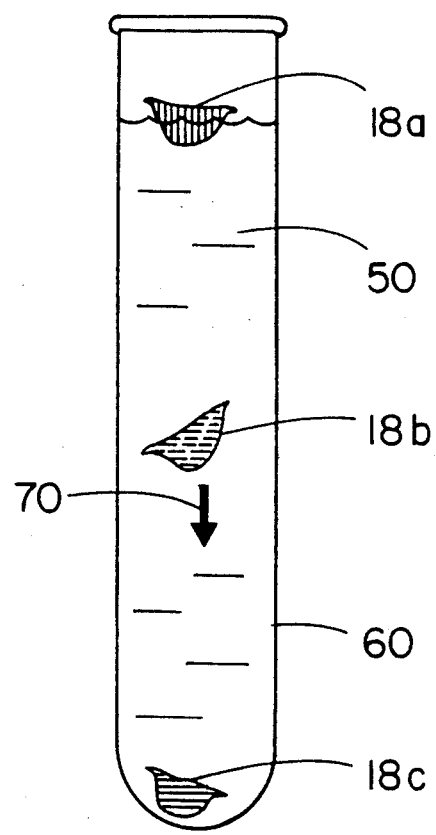
FIG. 5
FIG. 6

COMPARATIVE TEMPERATURE COMPENSATING SPECIFIC GRAVITY TEST APPARATUS

FIELD OF THE INVENTION

This invention relates to a comparative temperature compensating specific gravity test apparatus and more particularly to a device for providing quick and accurate field testing of liquids such as motor vehicle fuels.

BACKGROUND OF THE INVENTION

Various hydrometers are known for measuring the specific gravity of liquids. However, to date, none of these devices provides for inexpensive, convenient and yet highly accurate comparative field testing of specific gravity. Such field tests may be quite useful to military personnel for promptly determining if fuel taken from abandoned or captured motor vehicles or fuel supplies is suitable for use.

To be truly accurate, hydrometers must be temperature compensated. This is particularly important in the field where temperatures may vary from subarctic to tropical. To date, the majority of temperature compensating hydrometers have been intended for use in the laboratory or other controlled environment. They typically employ intricate and often delicate instrumentation, including thermometers and needle gauges, and are largely unsuited for the rough handling and dropping which may occur in the field. For example, glass thermometers are easily broken if dropped or handled roughly. Needles, shafts and other mechanisms may expand and contract under temperature extremes. As a result, such mechanisms can stick and further inaccuracies are introduced into the instrument.

One previous device attempts to achieve temperature compensation by employing a cell that is filled with a reference liquid. However, that device requires rather elaborate techniques to compensate for the weight, and therefore the density of the cell wall. Moreover, this device provides only an analog measure of specific gravity which must be read and analyzed. It does not provide a quick, comparative test that immediately tells even unsophisticated operators whether the test liquid is above a minimum required specific gravity.

Virtually the only known devices for providing comparative testing of specific gravity utilize styrofoam balls which float if the specific gravity of the test liquid is above that of the balls, but sink if the specific gravity of the liquid is below the level of the balls. Such devices may be acceptable for certain uses, such as the home testing of radiator and battery fluids. However, they typically provide no temperature compensation. The balls are filled with air which contracts or expands in response to the temperature of the test liquid. The specific gravity of the balls does not change proportionately with the specific gravity of the liquid and inaccurate measurements may be provided; for example, a ball may sink at one temperature and float at a second temperature. Such devices are therefore impractical when a highly accurate indication of specific gravity is required.

SUMMARY OF THE INVENTION

It is therefore an object of this invention to provide an improved apparatus and method for performing prompt, convenient and yet highly accurate comparative tests for specific gravity;

It is a further object of this invention to provide a comparative specific gravity test device and a method of utilizing the device which achieve prompt and precise temperature compensation without requiring elaborate structure or procedures;

It is a further object of this invention to provide a comparative temperature compensating specific gravity test device which is simpler and less expensive to construct than prior devices and which requires virtually no maintenance or repair;

It is a further object of this invention to provide a comparative temperature compensating specific gravity test device which is rugged, light weight and portable and which is particularly suited for use in the field.

This invention results from the realization that a simpler and yet more accurate comparative temperature compensating specific gravity tester may be achieved by utilizing a reference liquid that has substantially the same thermal expansion characteristic as that of the test liquid and which is enclosed by a highly pliable, sealed container which has a mass that is negligible compared to the mass of the reference liquid. This permits the mass of the compliant container to be largely disregarded and eliminates the need for elaborate structure and techniques to compensate for the container mass.

This invention features a comparative temperature compensating specific gravity test apparatus, including means for holding a test liquid. There is an indicator float element having a predetermined specific gravity and including a pliable, sealed container that is substantially free of contained gas. A reference liquid fills the container and has a thermal expansion characteristic which is substantially the same as that of the test liquid. The container has a mass which is negligible relative to the mass of the reference liquid. The indicator float element is freely suspendable in the test liquid such that floating of the float element indicates that the test liquid has at least the predetermined specific gravity and sinking of the float element indicates that the test liquid has less than the predetermined specific gravity.

In a preferred embodiment the mass of the container is no greater than 1% of the mass of the reference liquid. The container may include walls which are sufficiently thin to provide the float element with a generally amorphous shape. Such walls are preferably no greater than 0.002" thick. The float element may include indicia means to allow for visual monitoring of the element. Such indicia means may include a dye that is mixed with the reference liquid within the container. The container may include a synthetic resin laminate and may further have a peripheral seal.

The means for holding may include an elongate chamber having transparent means which permit monitoring of the float element. Indicator means may be displayed on the chamber for indicating whether or not the test liquid has at least the predetermined specific gravity. The chamber may include an entrance and a releasable closure may be provided for selectively covering and uncovering the entrance to the chamber. Grid means may be provided on the inside wall of the chamber opposite the transparent means to provide a measure of the turbidity of the test fluid.

The invention further features a method for comparatively testing the specific gravity of a test liquid. This method specifically comprises the steps of employing an indicator float element as described above and freely suspending that float element in a homogenous test liquid. The float element is then monitored. If it floats, the test liquid has at least the predetermined specific gravity; if the float element sinks, the test liquid is below the predetermined specific gravity.

DISCLOSURE OF PREFERRED EMBODIMENTS

Other objects, features and advantages will result from the following description of preferred embodiments and the accompanying drawings, in which FIG. 1 is an elevational front view of a preferred specific gravity test apparatus of this invention;

FIG. 2 is a plan view of the indicator float element;

FIG. 3 is a side elevational view of the float indicator element;

FIG. 4 is a partial, sectional and enlarged view of the laminar construction of the float element;

FIG. 5 is a front elevational view of the test apparatus wherein the test liquid is below the predetermined specific gravity level; and FIG. 6 is a front elevational view of an alternative specific gravity test device that utilizes a number of indicator float elements.

There is shown in FIG. 1 a comparative temperature compensating specific gravity test apparatus 10. The apparatus includes an elongate chamber 12 that is constructed of rugged plastic or similar material. Chamber 12 may be tubular or have various other shapes. The specific shape and size of the chamber are not limitations of this invention. Although chamber 12 is shown by itself, in alternative embodiments the chamber may be attached to or associated with other testing apparatus. The lower end of chamber 12 includes an entrance, not shown, through which fuel or other liquid L to be tested may be introduced and removed. A cap or closure 14 is releasably attached to chamber 12 by a flexible strap 16. In FIG. 1, closure 14 is shown covering the entrance so that test liquid L is held within chamber 12. To empty liquid 12, closure 14 is opened and the liquid is emptied through then entrance in the bottom of the chamber.

Chamber 12 includes a transparent forward face 15. A reference line 17 and "GO" and "NO GO" indicator marks 19 and 21, respectively, are printed on the opposite inside wall of the chamber. Also printed on that wall is a rectangular grid 23. These markings assist in testing fuels from captured or abandoned vehicles, in the manner described more fully below.

An indicator float element 18 having a predetermined specific gravity of, for example 0.78, is disposed in chamber 12. More particularly, element 18 is freely suspended in a homogeneous sample of liquid L. No other liquids are added to the chamber.

Float indicator element 18 is shown and described alone in FIGS. 2 through 4. The float element includes a thin walled, sealed container 20 which is highly pliable and impervious to air. The container is filled with a reference liquid 22. The reference liquid has a thermal expansion characteristic that is substantially the same as the thermal expansion characteristic of the test liquid L. For example, if a hydrocarbon fuel is being tested, liquid 22 will comprise various hydrocarbons such as kerosene, decane and hexane. If the specific gravity of salt water is to be tested, a float element is employed that includes salt water as a reference liquid. As a result, the density of liquid 22 changes proportionately to the density of liquid L when the temperature of the liquids increases or decreases.

Liquid 22 completely fills container 20 so that the container is substantially free of trapped air or other gases. Because such trapped air expands or contracts differently than the test liquid, (e.g. has a different thermal expansion characteristic), its presence tends to result in inaccurate temperature compensation. The sealed, impervious nature of container 20 prevents unwanted air from entering the container so that this effect is avoided.

The mass of container 20 is negligible relative to the mass of reference liquid 22. Preferably the mass of container 20 is less than 1% of the mass of liquid 22. This virtually eliminates any effect that the mass of container 20 otherwise has on the density or specific gravity of float element 18.

As best shown in FIG. 4, container 20 includes an upper piece of plastic 30 and a lower piece of plastic 32. Each of pieces 30 and 32 comprises a laminate including an outer layer 34 of a material such as polyester or nylon which is not heat sensitive, and an inner layer 36 of a thermoplastic, such as polyethylene. The respective layers 36 of polyethylene are heat sealed together at seal S along the peripheral edge of element 18. In FIG. 4 the peripheral edge has been separated for clarity. Reference liquid 22 fills the pocket formed by upper and lower pieces 30 and 32. The walls of container 20 are quite thin, preferably 0.002" or less, so that pliable float element 18 maintains a generally amorphous shape when suspended in liquid L. This allows element 18 to freely contract and expand within liquid L due to expansion or contraction of liquid 22 alone. The container walls have virtually no affect.

In operation, hydrocarbon liquid L whose specific gravity is to be comparatively tested is introduced through the entrance of chamber 12 and the chamber is uprighted into the position shown in FIG. 1. Indicator float element 18 is thereby suspended in liquid L. The float element may be placed into the chamber either before or after liquid L is introduced or permanently captured in the chamber.

After chamber 12 is uprighted, the operator pauses for a brief period so that the temperatures of float element 18 and liquid L may equalize. Because liquid 22 and liquid L have the same thermal expansion characteristic, and because the thermal expansion characteristic of container 20 may be disregarded, the apparatus 10 is temperature compensated. The density or specific gravity relationship between the float element and the test liquid remains constant, regardless of temperature. If, float element 18 remains floated at the top of liquid L, as shown in FIG. 1, this indicates that liquid L is exerting buoyancy on float element 18 and that the specific gravity of test liquid L is greater than the known specific gravity of float element 18.

The markings on apparatus 10 are particularly helpful for testing fuels. Monitoring the float element through transparent face 15, the operator notes that the float element remains above center line 17, within the "GO" region 19. This indicates that the test fuel liquid L has an acceptable specific gravity and may be used. Such observation is assisted by providing float element 18 with visual indicia, such as coloring. As shown in FIG. 1 this color may be black. Alternatively, any other visual colors may be utilized. This color may be added to float element 18 by dyeing reference liquid 22.

If, alternatively, the specific gravity of test liquid L is below that of float element 18, the test liquid does not exert a positive buoyancy upon element 18 and the element sinks, as shown in FIG. 5. The operator notes that the indicator drops below center line 17 into the region 21 labeled "NO GO". This indicates that the liquid fuel being tested is unacceptable for use.

Grid 23 permits the operator to monitor the turbidity of liquid L at the same time he is testing the liquid for specific gravity. If the grid, which is printed on the inside wall of chamber 12, is visible through test liquid L then the test liquid has an acceptable level of turbidity. If however, the grid is not visible, then the turbidity is unacceptably high.

When apparatus 10 is used to test the specific gravity of various hydrocarbon fuels, indicator float element 18 is provided with a predetermined specific gravity of 0.78. For element 18 to float in a test fuel, the fuel must have a specific gravity of at least 0.78. When compared to water at 40 degrees centigrade, it has been determined that the apparatus of this invention is precise to within 0.01 sp G. A float element with specific gravity of 0.78 sinks in a test liquid having a specific gravity of 0.77 and floats in a liquid with a specific gravity of 0.78 or higher. Between 0.77 and 0.78 sp G of test liquid float element 18 tends to drift slowly in the test liquid toward its ultimate destination on the surface or at the bottom.

A more precise measurement of specific gravity may be provided by employing a plurality of float elements, 18a, 18b and 18c, FIG. 6. In this embodiment, test liquid 50 comprising a hydrocarbon fuel is collected in a tube 60. The tube further accommodates three indicator float elements 18a, 18b and 18c. Float element 18a is constructed, as previously described, to have a predetermined specific gravity of 0.77; float element 18b has a specific gravity of 0.78; and float element 18c has a specific gravity of 0.79. In this embodiment, the float elements are introduced into test liquid 50 through an opening in the top of tube 60. Float element 18a remains floating at the top of liquid 50. Float element 18c rapidly drops to the bottom of tube 60 and float element 18b sinks more slowly to the bottom, in the direction of arrow 70. This indicates that test liquid 50 has a specific gravity greater than that of float element 18a, i.e. 0.77, but less than that of float element 18b, i.e. 0.78. As a result, the operator quickly determines that the specific gravity is between 0.77 and 0.78. Float elements 18a, 18b and 18c are dyed red, grey and blue respectively, so that the operator may quickly identify the respective float elements and determine the comparative specific gravity of the test liquid relative to each.

In alternative embodiments of this invention, a portable chamber or tube for holding the test liquid is not required. The operator may simply bring a float element having a known specific gravity into the field and introduce it into a homogeneous specimen of test liquid having substantially the same thermal expansion characteristic. The test sample can be held in a drum, can, bottle or other holder. As long as the operator is able to monitor the float element within the test sample he can judge the comparative specific gravity of sample liquid. If the float element remains floating, the specimen has specific gravity which is at least equal to that of the float element. If, however, the float element sinks, then the specific gravity of the specimen is below that of the float element. Because the relative specific gravities of the float elements and the test liquid remain constant the test is accurate at all temperatures.

Accordingly, the apparatus of this invention permits quick and accurate temperature compensated testing for specific gravity of liquids. This apparatus is particularly suited for use in the field, as it does not require intricate mechanisms or delicate breakable parts. Because it provides for a quick comparative test, working with numbers and more complex calculations are not required. Even unsophisticated personnel can rapidly determine if the test liquid is above or below a desired specific gravity.

Although specific features of the invention are shown in some drawings and not in others, this is for convenience only, as each of the features may be combined with any or all of the other features in accordance with the invention.

Other embodiments will occur to those skilled in the art and are within the following claims:

What is claimed is:

1. A comparative temperature compensating specific gravity test apparatus comprising:
   means for holding a test liquid; and
   an indicator float element having a predetermined specific gravity and including a pliable sealed container that is substantially free of contained gas and a reference liquid that fills said container; said reference liquid having a thermal expansion characteristic which is substantially the same as that of said test liquid; said container having a mass which is negligible relative to the mass of said reference liquid; and said indicator float element being disposed in said test liquid free of any attachment such that floating of said float element indicates that said test liquid has at least said predetermined specific gravity and sinking of said float element indicates that said test liquid has less than said predetermined specific gravity.

2. The apparatus of claim 1 in which said mass of said container is no greater than one percent of the mass of said reference liquid.

3. The apparatus of claim 1 in which said container includes walls which are sufficiently thin to provide said float element with an amorphous shape.

4. The apparatus of claim 3 in which said walls are no greater than 0.002 inches thick.

5. The apparatus of claim 1 in which said float element includes indicia means for permitting visual monitoring of said element.

6. The apparatus of claim 5 in which said indicia means include a dye that is mixed with said reference liquid.

7. The apparatus of claim 1 in which said container includes a synthetic resin laminate.

8. The apparatus of claim 1 in which said container includes a peripheral seal;

9. The apparatus of claim 1 in which said means for holding include an elongate chamber having transparent means which permit monitoring of said float element.

10. The apparatus of claim 9 in which grid means are formed on an inside wall of said chamber opposite said transparent means for providing an indication of the turbidity of said test liquid.

11. The apparatus of claim 9 in which said sealed chamber includes an entrance and further including a releasable closure for selectively covering and uncovering said entrance to the chamber.

12. The apparatus of claim 1 in which said means for holding include means for indicating whether or not the test liquid has at least said predetermined specific gravity.

13. A temperature compensating indicator float element for comparatively testing the specific gravity of a test liquid comprising:
   a pliable sealed container that is substantially free of contained gas; and
   a reference liquid that fills said container and has a thermal expansion characteristic which is substantially the same as that of said test liquid; said container having a mass which is negligible relative to the mass of said reference liquid;
   whereby said float element exhibits a predetermined specific gravity and is disposed in a test liquid free of any attachment such that floating of said float element indicates that said test liquid has at least said predetermined specific gravity and sinking of said float element indicates that said test liquid has less than said predetermined specific gravity.

14. The element of claim 13 in which said mass of said container is no greater than 1% of the mass of said reference liquid.

15. The apparatus of claim 13 in which said container includes walls which are sufficiently thin to provide said float element with an amorphous shape.

16. The apparatus of claim 15 in which said walls are no greater than 0.002 inches thick.

17. The apparatus of claim 13 in which said float element includes indicia means for permitting visual monitoring of said element.

18. The apparatus of claim 17 in which said indicia means include a dye that is mixed with said reference liquid.

19. The apparatus of claim 13 in which said container includes a synthetic resin laminate.

20. The apparatus of claim 13 in which said container includes a peripheral seal.

21. A method for comparatively testing the specific gravity of a liquid comprising the steps of:
   employing an indicator float element having a predetermined specific gravity and including a pliable sealed container that is substantially free of contained gas and a reference liquid that fills said container; said container having a mass which is negligible relative to the mass of said reference liquid;
   introducing said indicator float element free of any attachment in a homogeneous test liquid having a thermal expansion characteristic that is substantially the same as that of said indicator float element; and
   monitoring said indicator float element; whereby floating of said float element indicates that said test liquid has at least said predetermined specific gravity and sinking of said float element indicates that said test liquid has less than said predetermined specific gravity.

22. A comparative temperature compensation specific gravity test apparatus comprising:
   means for holding a test liquid; and
   an indicator float element having a predetermined specific gravity and including a pliable sealed container that is substantially free of contained gas and a reference liquid that fills said container; said reference liquid having a thermal expansion characteristic which is substantially the same as that of said test liquid; said container having a mass which is negligible relative to the mass of said reference liquid; and said indicator float element being freely suspendable in said test liquid such that floating of said float element indicates that said test liquid has at least said predetermined specific gravity and sinking of said float element indicates that said test liquid has less than said predetermined specific gravity; said float element including indicia means that include a dye mixed with said reference liquid for permitting visual monitoring of said element.

23. A temperature compensating indicator float element for comparatively testing the specific gravity of a test liquid comprising:
   a pliable sealed container that is substantially free of contained gas;
   a reference liquid that fills said container and has a thermal expansion characteristic which is substantially the same as that of said test liquid, said container having a mass which is negligible relative to the mass of said reference liquid;
   and indicia means that include a dye mixed with said reference liquid for permitting visual monitoring of said float element;
   whereby said float element exhibits a predetermined specific gravity and is freely suspendable in a test liquid such that floating of said float element indicates that said test liquid has at least said predetermined specific gravity and sinking of said float element indicates that said test liquid has less than said predetermined specific gravity.

* * * * *